United States Patent [19]

Nemec

[11] 4,153,061

[45] May 8, 1979

[54] ELECTROTHERAPEUTIC APPARATUS

[76] Inventor: Hans Nemec, Ausstrasse 1, Rankweil, Austria

[21] Appl. No.: 843,953

[22] Filed: Oct. 20, 1977

[30] Foreign Application Priority Data

Oct. 21, 1976 [AT] Austria .................. 7848/76

[51] Int. Cl.$^2$ .............................................. A61N 1/36
[52] U.S. Cl. ................................. 128/420 A; 128/422
[58] Field of Search ........... 128/420 A, 420 R, 419 R, 128/421, 422

[56] References Cited

U.S. PATENT DOCUMENTS

| | | | |
|---|---|---|---|
| 2,622,601 | 12/1952 | Nemec | 128/422 |
| 3,096,768 | 7/1963 | Griffith, Jr. | 128/420 A |
| 3,774,620 | 11/1973 | Hansjurgen | 128/420 A |
| 3,958,577 | 5/1976 | Rodler | 128/420 A |

FOREIGN PATENT DOCUMENTS 2159437  4/1973  Fed. Rep. of Germany ...... 128/420 A

Primary Examiner—Lee S. Cohen
Attorney, Agent, or Firm—Montague & Ross

[57] ABSTRACT

Electrical stimulation of muscles and nerves of a human or animal body is brought about by passing two or more carrier frequencies, in a medium range of about 1,000 to 10,000 Hz., along separate but intersecting paths through the body to be treated. Each carrier is amplitude-modulated by a low frequency, preferably not exceeding about 200 Hz., which affords local stimulation in the vicinity of the body-contacting electrodes as well as internal stimulation due to the beat frequencies generated by the modulated carriers.

10 Claims, 2 Drawing Figures

ELECTROTHERAPEUTIC APPARATUS

FIELD OF THE INVENTION

My present invention relates to a method of electrotherapeutically treating a human or animal body as well as to an apparatus for carrying out this method.

BACKGROUND OF THE INVENTION

In my prior U.S. Pat. No. 2,622,601 I have described an apparatus of this general type wherein currents of a medium frequency, in a range between 1,000 and 10,000 Hz., are passed over separate but intersecting paths through a body to be treated, with generation of low-frequency beats in the region of the intersection. As discussed in that prior patent, alternating currents in this medium-frequency range have no significant effect upon muscle and nerve tissues whereas frequencies below this range, especially those on the order of 100 Hz., act as stimulators. Thus, the heterodyning of two slightly different medium frequencies in the interior of the body gives rise to low frequencies having the desired therapeutic effect.

There are also instances in which a stimulation closer to the surface of the body is useful, i.e. in the vicinity of the skin-contacting electrodes between which the alternating currents are transmitted. While the medium frequencies will be ineffectual in this regard, it has already been propsed to use a carrier frequency amplitude-modulated by a low frequency for such purpose. Reference in this connection may be made to my Austrial Pat. No. 296,496 as well as Austrian Pat. Nos. 165,657, 203,147 and 332,528.

As further discussed in my prior U.S. Pat. No. 2,662,601, continued application of body-stimulating low frequencies results in an accommodation or fatigue phenomenon, i.e. a decline of the original stimulating effect. To avoid this inconvenience, it is necessary to vary the intensity of the current at a relatively slow rate, generally with a period upwards of one second. In my recently issued U.S. Pat. No. 4,023,574. I have disclosed a system which achieves this result by the interaction of three frequencies of at least 1,000 Hz, two of these frequencies differing from each other by a value of 50 to 100 Hz. whereas the third one differs from one of the first two frequencies or from their arithmetic mean by 1 Hz. or less. The system of this latter patent also has no significant therapeutic effect in the vicinity of the body-contacting electrodes.

OBJECTS OF THE INVENTION

An object of my present invention, therefore, is to provide an electrotherapeutical-treatment method providing controlled stimulation both near the surface and in the interior of a human or animal body.

A related object is to provide a simple apparatus for carrying out this method.

SUMMARY OF THE INVENTION

According to an aspect of my present invention, a first and a second carrier frequency in the aforementioned medium range of about 1,000 to 10,000 Hz. are modulated with low frequencies (of identical or different magnitudes) below that range. The resulting amplitude-modulated carrier frequencies are passed over separate but intersecting paths through the body to be treated, thus giving rise to a rather broad spectrum of beat frequencies inside the body. With suitable choice of the carrier and modulating frequencies, some of these beat frequencies (due to slow relative phase shifts of the modulated carriers) have values of 1 Hz. or less to provide the desired antifatiguing effect.

Advantageously, the two carrier frequencies differ from each other by a value less than that of the modulating frequency or frequencies whereby their respective frequency bands overlap to a considerable extent. I prefer to keep this frequency difference between about 5 and 25 Hz. in order to stimulate vibrations and shocks within the tissues designed to intensify the blood circulation. With modulating frequencies between about 40 and 100 Hz., significant myomotoric effects can be achieved near the point of application of a supply electrode. Higher modulating frequencies, between about 100 and 200 Hz., may be used for purposes of sedation and analgesis.

A further control of the therapeutic effect can be exercised by the choice of the depth of modulation of each carrier. If this modulation is less than 100%, a beat frequency equal to the difference of the two carrier frequencies will always be in existence.

According to another aspect of my invention, the carriers and their modulating frequencies are separately generated by respective oscillators and combined in amplitude modulators before being fed to respective electrode pairs.

BRIEF DESCRIPTION OF THE DRAWING

A representative embodiment of my invention will now be described in detail with reference to the accompanying drawing in which.

SPECIFIC DESCRIPTION

Figure 1:
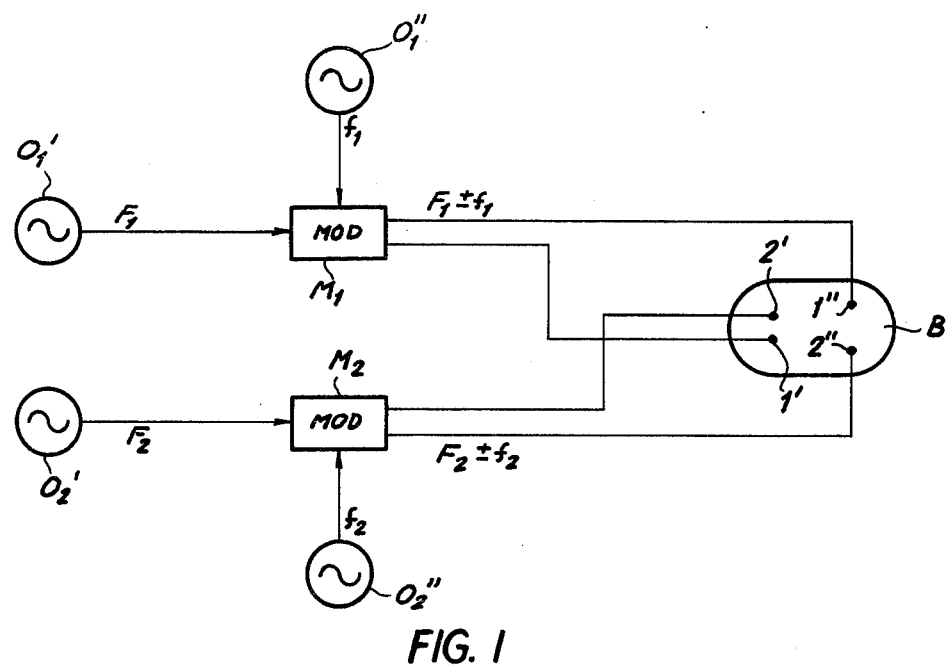
FIG. 1 is a block diagram of an apparatus according to the invention.

In FIG. 1 I have shown two oscillators $O_1'$ and $O_2'$, generating respective carrier frequencies $F_1$ and $F_2$ in the above-discussed medium range, and two other oscillators $O_1''$, $O_2''$ generating frequencies $f_1$ and $f_2$ well below that range. A first modulator $M_1$, receiving the outputs of oscillators $O_1'$ and $O_1''$, emits an amplitude-modulated carrier frequency $F_1 \pm f_1$ which is passed through a body B by way of a pair of electrodes $1'$ and $1''$. In a similar manner, a modulator $M_2$ has input connections to oscillators $O_2'$ and $O_2''$ for synthesizing an amplitude-modulated carrier $F_2 \pm f_2$ transmitted through body B with the aid of a pair of electrodes $2'$ and $2''$. It will be noted that the current paths established by these electrode pairs are different but intersect within body B.

Figure 2:
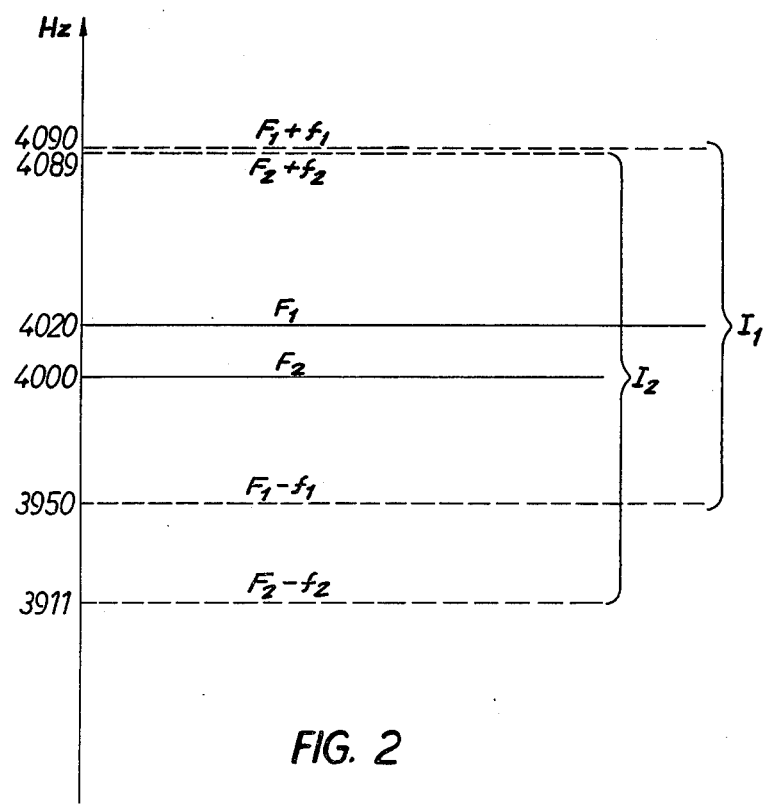
FIG. 2 is a graph illustrating the frequency distribution in the system of FIG. 1.

In FIG. 2 I have shown, by way of example, the carrier frequencies as having values of $F_1 = 4020$ Hz. and $F_2 = 4000$ Hz., with modulating frequencies $f_1 = 70$ Hz. and $f_2 = 89$ Hz. This results in a current $I_1$ of 140-Hz. bandwidth and a current $I_2$ of 178-Hz. bandwidth, the two bands overlapping for 139 Hz. It will also be noted that the upper sideband frequencies $F_1 + f_1$ and $F_2 + f_2$ of the two modulated carriers differ by only 1 Hz. so as to generate a beat with a period of one second. This period could be increased, e.g. to about six seconds, by placing these sideband frequencies still closer to each other.

It will thus be apparent that the six frequency components illustrated in FIG. 2 will produce a large number of beat frequencies, though some of those could be eliminated by the selection of coincident sidebands and- /or by the supression of one or both carriers. Naturally, the method according to my invention can be expanded with the use of more than two carrier frequencies.

I claim:

1. A method of electrotherapeutically treating a human or animal body, comprising the steps of:
generating a first and a second carrier frequency in a range between substantially 1,000 and 10,000 Hz.;
amplitude-modulating said carrier frequencies with respective low frequencies of up to about 200 Hz.; and
simultaneously passing the amplitude-modulated carrier frequencies over separate but intersecting paths through the body to be treated for stimulating selected surface areas of said body by the amplitude modulation while producing stimulation-inducing beat frequencies in the interior of said body at the intersection of said paths.

2. A method as defined in claim 1 wherein said carrier frequencies differ from each other by a value less than the magnitude of said low frequencies.

3. A method as defined in claim 2 wherein said value lies between substantially 5 and 25 Hz.

4. A method as defined in claim 3 wherein said low frequencies lie between substantially 40 and 100 Hz.

5. A method as defined in claim 4 wherein said amplitude-modulated carrier frequencies have sideband frequencies lying within substantially 1 Hz. from each other.

6. An electrotherapeutic apparatus comprising:
first oscillator means generating a pair of carrier frequencies in a range between substantially 1,000 and 10,000 Hz.;
second oscillator means generating at least one modulating frequency of up to about 200 Hz;
first modulator means with inputs connected to respective outputs of said first and second oscillator means for producing a first amplitude-modulated carrier;
second modulator means with inputs connected to respective outputs of said first and second oscillator means for producing a second amplitude-modulated carrier;
first electrode means connected to an output of said first modulator means and positionable on said body for passing said first amplitude-modulated carrier therethrough; and
second electrode means connected to an output of said second modulator means and positionable on said body for passing said second amplitude-modulated carrier therethrough over a path intersecting the path of said first amplitude-modulated carrier for stimulating selected surface areas of said body by the amplitude modulation while producing stimulation-inducing beat frequencies in the interior of said body at the intersection of said paths.

7. An apparatus as defined in claim 6 wherein said carrier frequencies differ from each other by a value less than the magnitude of said modulating frequency.

8. An apparatus as defined in claim 7 wherein said value lies between substantially 5 and 25 Hz.

9. An apparatus as defined in claim 8 wherein said modulating frequency lies between substantially 40 and 100 Hz.

10. An apparatus as defined in claim 9 wherein said second oscillator means generates different modulating frequencies respectively fed to said first and second modulator means, said first and second amplitude-modulated carriers having sideband frequencies which lie within substantially 1 Hz. from each other.

* * * * *